United States Patent [19]

Kadaba

[11] Patent Number: 4,511,572
[45] Date of Patent: Apr. 16, 1985

[54] TRIAZOLINE ANTICONVULSANT DRUGS

[75] Inventor: Pankaja K. Kadaba, Lexington, Ky.

[73] Assignee: The University of Kentucky Research Foundation, Lexington, Ky.

[21] Appl. No.: 476,792

[22] Filed: Mar. 18, 1983

[51] Int. Cl.³ .................... A61K 31/44; A61K 31/41; A61K 31/49
[52] U.S. Cl. .................................................. 514/340
[58] Field of Search ......................................... 424/203

[56] References Cited

U.S. PATENT DOCUMENTS

| | | | |
|---|---|---|---|
| 3,470,196 | 9/1969 | Harvey | 260/308 |
| 3,965,094 | 6/1976 | Claussen et al. | 260/240 C |
| 4,013,441 | 3/1977 | Bianchetti et al. | 71/92 |
| 4,148,803 | 4/1979 | Wehrmeister | 260/308 A |

FOREIGN PATENT DOCUMENTS 2070607A  9/1981  United Kingdom .

OTHER PUBLICATIONS

Kadaba, P. K., And Triplett, J., "Heterocycles, an Internat'l Journal for Reviews and Comm. in Heterocyclic Chem.," vol. 9, No. 3, 1978, pp. 243-246.
Kadaba, P. K., "Synthesis, Internat'l Journal of Methods in Synthetic Organic Chem.," No. 9, Sep. 1978, pp. 694-695.
Kadaba, P. K., "Pestic. Sci.," 1974, vol. 5, pp. 255-258.
Kadaba, P. K., "Journal of Pharmaceutical Sciences," vol. 59, No. 8, 1970, pp. 1190-1191.
Kadaba, P. K., and Edwards, J., "Journal of Organic Chemistry," vol. 26, 1961, pp. 2331-2335.
Kadaba, P. K., "Tetrahedron," vol. 22, 1966, pp. 2453-2460.
Kadaba, P. K., and Fannin, N., "Journal of Heterocyclic Chemistry," vol. 4, 1967, pp. 301-304.
Kadaba, P. K., "Journal of Heterocyclic Chemistry," vol. 6, 1969, pp. 587-589.
Kadaba, P. K., "Tetrahedron," vol. 25, 1969, pp. 3053-3066.
Kadaba, P. K., "Synthesis, International Journal of Methods in Synthetic Organic Chemistry," No. 2, Feb. 1973, pp. 71-84.
Kadaba, P. K., "Journal of Heterocyclic Chemistry," vol. 12, 1975, pp. 143-146.
Kadaba, P. K., "Journal of Heterocyclic Chemistry," vol. 13, 1976, pp. 1153-1154.

Primary Examiner—Stanley J. Friedman
Attorney, Agent, or Firm—Lowe, King, Price & Becker

[57] ABSTRACT

Anticonvulsant compositions comprise as the active ingredient a compound selected from the group consisting of those of the formulae:

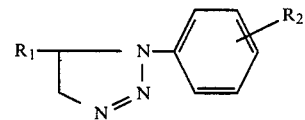

wherein $R_1$ is o-chlorophenyl, o-nitrophenyl, 2,4- or 2,6-dichlorophenyl, 4-pyridyl, 2-pyridyl, or 2-quinolyl, and $R_2$ is hydrogen, m- or p-trifluoromethyl, p-methyl, p-ethyl, m- or p-chloro, m-nitro, p-bromo, p-fluoro or p-COOR$_3$ wherein $R_3$ is lower alkyl of 1 to 4 carbon atoms. The compositions are administered to mammals in an amount to provide a dosage amount ranging from about 30 mg/kg to 300 mg/kg.

13 Claims, No Drawings

TRIAZOLINE ANTICONVULSANT DRUGS

TECHNICAL FIELD

This invention relates to $\Delta^2$-1,2,3-triazolines and their use as a new and novel class of anticonvulsant drugs, and more particularly relates to certain additional new $\Delta^2$-1,2,3-triazolines, their methods of preparation, and compositions for their use in the treatment of convulsive disorders.

BACKGROUND ART

Studies over the past 15 years suggest that the prevailing rate of epilepsy in the United States is between 5 and 20 per 1000, and recent estimates drawn from population surveys indicate that the higher rates are closer to the true prevalence. This means that 1 to 4 million Americans suffer from some form of epilepsy. For certain types of seizures there are no specific drugs available; for seizures that are controlled with currently available therapy, a new drug may allow a reduction in the toxic side effects. Despite these facts, between 1960 and 1974, no new anticonvulsant drug was marketed in the United States (with the exception of diazepam, which was marketed primarily as a minor tranquilizer) (Vida, J. A. "Anticonvulsants," Academic Press, New York, 1977). However, since the approval of carbamazepine in 1974 and clonazepam in 1975, and sodium dipropylacetate, eterobarb, mexiletine and others in 1977-1978, there has been a resurgence of interest in the development of better anticonvulsant drugs for the management of epilepsy. Also responsible for this renewed interest is the establishment of the Anticonvulsant Screening Project of the Antiepileptic Drug Development (ADD) Program of NINCDS (National Institute of Neurological and Communicative Disorders and Stroke) of NIH, in January, 1975.

In recent years hundreds of different heterocyclic compounds have been synthesized and screened for anticonvulsant activity. These include mostly five and six membered ring systems containing up to three or four heteroatoms and seven membered ring systems related to the diazepines. Among the nitrogen containing heterocycles, a considerable amount of work has been done in the areas of five membered rings bearing one or two nitrogen atoms.

Five membered rings with 3 or 4 nitrogen atoms that have been investigated, include mostly, 1,2,4-triazoles and some tetrazoles. Very little has been done on 1,2,3-triazoles (Popp, F. D., In "Anticonvulsants," J. A. Vida, Ed. Academic Press, New York, 1977). The literature indicates that to date there are no references to any published work relating to studies on the anticonvulsant activity of triazolines.

The 1,2,3-triazolines are a novel group of anticonvulsant compounds because their heterocyclic ring system is different from that of conventional anticonvulsant drugs. The presently marketed antiepileptic drugs, for the major part, have a dicarboximide function and/or a disubstituted quaternary carbon group (barbiturates, hydantoins, succinimides, oxazolidinediones) or closely related structure (primidone). On the other hand, the dicarboximide function, which contributes to the inherent hypnotic and sedative activity of the barbiturates and related compounds, is absent in the triazolines.

Triazolines including $\Delta^2$-1,2,3-triazolines, are known to some extent in the prior art, through applicant's own publications of work in this area. None of the triazolines, however, has been suggested heretofore for use as anticonvulsants.

As indicated, the present applicant has published a number of papers involving her work on triazolines. The following publications discuss primarily the use of triazolines as intermediates in providing a route for the synthesis of certain anilinopyridazines and pyrazoles, (Kadaba, P. K., and Triplett, J. "Heterocycles, An International Journal for Reviews and Communications in Heterocyclic Chemistry," Vol. 9, No. 3, 1978, pp. 243–246) and triazoles (Kadaba, P. K. "Synthesis, International Journal of Methods in Synthetic Organic Chemistry," No. 9: September, 1978, pp. 694–695.)

The following publications describe the results of screening or evaluation of triazolines for pesticide and herbicide properties. (Kadaba, P. K., "Pestic. Sci.," 1974, 5, pp. 255–258.) (Kadaba, P. K., "Journal of Pharmaceutical Sciences," Vol. 59, No. 8, 1970, pp. 1190–91.)

The following publications primarily describe procedures for the production of triazolines through cycloaddition of diazomethane to Schiff bases and solvent effects on this reaction as well as steric effects. (Kadaba, P. K., and Edwards, J. "Journal of Organic Chemistry, 26, 1961, pp. 2331–2335.) (Kadaba, P. K., "Tetrahedron, Vol. 22, 1966, pp. 2453–2460.) (Kadaba, P. K., and Fannin, N., "Journal of Heterocyclic Chemistry," 4, 1967, pp. 301–304.) (Kadaba, P. K., "Journal of Heterocyclic Chemistry, 6, 1969, pp. 587–589.) (Kadaba, P. K. "Tetrahedron, Vol. 25, 1969, pp. 3053–3066.) (Kadaba, P. K., "Synthesis, International Journal of Methods in Synthetic Organic Chemistry, No. 2: February, 1973, pp. 71–84.) (Kadaba, P. K., "Journal of Heterocyclic Chemistry, 12, 1975, pp. 143–146.) (Kadaba, P. K., "Journal of Heterocyclic Chemistry, 13, 1976, pp. 1153–54.)

In none of these publications, however, is there any disclosure of use of any of the 1,2,3 triazoline compounds as anticonvulsants.

SUMMARY OF THE INVENTION

It is accordingly one object of the present invention to provide certain triazolines as anticonvulsant drugs.

A further object of the present invention is to provide several new $\Delta^2$-1,2,3-triazolines and methods for their use in the treatment of convulsive disorders.

A still further object of the present invention is to provide anticonvulsant compositions containing as the essential ingredient certain $\Delta^2$-1,2,3-triazolines and use of these triazolines as antiepileptic drugs in the treatment of convulsive disorders such as epilepsy.

Other objects and advantages of the present invention will become apparent as the description thereof proceeds.

In satisfaction of the foregoing objects and advantages, there is provided by this invention anticonvulsant compositions comprising as the active ingredient, a compound selected from those of the following formulae:

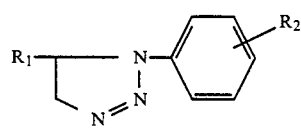

Wherein $R_1$ is o-chlorophenyl, o-nitrophenyl, 2,4- or 2,6-dichlorophenyl, 4-pyridyl, 2-pyridyl or 2-quinolyl, and $R_2$ is hydrogen, m- or p-trifluoromethyl, p-methyl, p-ethyl, p-fluoro, m- or p-chloro, p-bromo, m-nitro, or p-COOR$_3$ wherein $R_3$ is lower alkyl of one to four carbon atoms.

Also provided are methods for administration of the anticonvulsant compositions of this invention to mammals in the treatment of convulsive disorders such as epilepsy including petit mal and grand mal.

There is also provided by this invention certain new compounds which are useful as anticonvulsant drugs. These compounds may be characterized by the following general formulae:

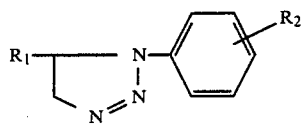

Wherein $R_1$ is 4-pyridyl, 2-pyridyl, orthochlorophenyl, 2,6-dichlorophenyl, or ortho-nitrophenyl, and $R_2$ is p-fluoro, p-bromo, m- or p-trifluoromethyl, p-ethyl, m-chloro or hydrogen.

DESCRIPTION OF PREFERRED EMBODIMENTS

As indicated above, this invention relates to certain 1,2,3-triazolines which are useful as anticonvulsants. The triazolines of this invention are to be named as $\Delta^2$-1,2,3-triazolines, or as 1H-4,5-dihydro-1,2,3-triazoles. The triazolines of this invention are substituted in the 1 and 5 positions by aryl or heterocyclic groups which may also contain substituents. The triazoline compounds of this invention have potent to moderate anticonvulsant activity as antiepileptic drugs in the treatment of convulsive disorders such as petit mal (absence seizures) and grand mal (major motor seizures).

In one aspect of the invention, it relates to novel anticonvulsant compositions which comprise as the active ingredient a compound selected from those of the following formulae:

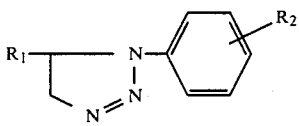

Wherein $R_1$ is o-chlorophenyl, o-nitrophenyl, 2,4- or 2,6-dichlorophenyl, 4-pyridyl, 2-pyridyl or 2-quinolyl, and $R_2$ is hydrogen, m- or p-trifluoromethyl, p-methyl, p-ethyl, p-fluoro, m- or p-chloro, p-bromo, m-nitro, or p-COOR$_3$ wherein $R_3$ is lower alkyl of one to four carbon atoms.

In a further aspect of the present invention, new compounds are provided which have anticonvulsant activity and which are of the following general formulae:

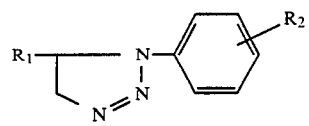

In the above formulae, $R_1$ is 2-pyridyl, 4-pyridyl, ortho-chlorophenyl, or ortho-nitrophenyl and $R_2$ is p-fluoro, m- or p-trifluoromethyl, p-ethyl, or m-chloro and when $R_1$=2,6-dichlorophenyl, $R_2$ can be p-bromo and when $R_1$=2-pyridyl, $R_2$ can be hydrogen.

There is further provided by this invention methods for administration of the anticonvulsant composition to mammals including animals and humans.

The triazolines of this invention may be prepared by the reaction of diazomethane with Schiff bases as described, for example, by Mustafa, A., (J. Chem. Soc.), 234 (1949), and by Buckley, G. D., (J. Chem. Soc), 1850, (1954). Further methods of preparation involving 1,3-dipolar cycloaddition reactions are described in the applicant's own publications in Kadaba, et al. (J. Org. Chem., 26, 2331 (1961), by Kadaba in "Tetrahedron," 22, 2453 (1966), by Kadaba in "Tetrahedron," 25, 3053 (1969) and J. Heterocyclic Chem., 12, 143, (1975). This reaction proceeds generally in accordance with the following equation.

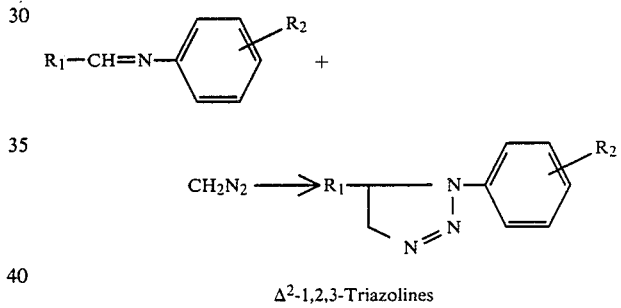

$\Delta^2$-1,2,3-Triazolines

In the above equation $R_1$ and $R_2$ are as defined above.

Kinetic studies on solvent effects of this reaction indicate that protic solvents such as water have a general accelerating effect on the reaction and by carrying out the addition reaction in an aqueous dioxane solution, high yields of triazolines are produced.

As pointed out, the triazoline compounds and resulting anticonvulsant compositions of this invention are useful in the treatment of convulsive disorders. The potency of the compounds range from those which are very potent to those of moderate potency. A series of triazolines of this invention has been evaluated in Phase I anticonvulsant screening using two seizure models in the mouse, the maximal electro-shock seizure (MES) test and the subcutaneous pentylenetetrazole (Metrazole) seizure threshold (scMet) test. These two methods of seizure provocation reliably elicit well characterized seizure phenomena (Chen. G., et al. Proc. Soc. Exp. Biol. Med., 87, 334 (1954), and together have been shown sufficient to identify all compounds known to demonstrate anticonvulsant activity in other tests. Based on the Phase I screening results, the compound to be tested is placed in one of three categories. Those failing to demonstrate anticonvulsant activity at doses up to 300 mg/kg are considered inactive. Class II compounds show anticonvulsant activity at doses greater than 100 mg/kg or show activity at 100 mg/kg which is not reinforced by similar activity at 300 mg/kg. Thus compounds of class or group II demonstrate anticonvulsant activity without signs of neurological deficit, but do not have significant potency. The Class I compounds are those which are most promising as anticonvulsants. They demonstrate anticonvulsant activity in either the MES test or the ScMet test, or both at doses of 100 mg/kg or 30 mg/kg without signs of neurological deficit and thus have an estimated protective index of greater than 1.

The following table presents the results of these tests with respect to certain compounds of the present invention. This Table 1 identifies the specific compounds tested, by chemical name and provides the anticonvulsant activity based on classification in Group I or Group II.

TABLE 1

| Compound | Anticonvulsant Activity Group Classification |
|---|---|
| 1. 1-m-trifluoromethylphenyl-5-(o-chlorophenyl)-$\Delta^2$-1,2,3-triazoline | II |
| 2. 1-(p-Trifluoromethylphenyl-5-(o-chlorophenyl)-$\Delta^2$-1,2,3-triazoline | II |
| 3. 1-(p-Ethylphenyl)-5-(o-chlorophenyl)-$\Delta^2$-1,2,3-triazoline | II |
| 4. 1-(m-Chlorophenyl)-5-(o-nitrophenyl)-$\Delta^2$-1,2,3-triazoline | II |
| 5. 1-(m-Nitrophenyl)-5-(2,4-dichlorophenyl)-$\Delta^2$-1,2,3-triazoline | II |
| 6. 1-(p-Bromophenyl)-5-(2,6-dichlorophenyl)-$\Delta^2$-1,2,3-triazoline | II |
| 7. 1-(Phenyl)-5-(4-pyridyl)-$\Delta^2$-1,2,3-triazoline | II |
| 8. 1-(p-Ethoxycarbonyl)-5-(4-pyridyl)-$\Delta^2$-1,2,3-triazoline | II |
| 9. 1-(p-Chlorophenyl)-5-(4-pyridyl)-$\Delta^2$-1,2,3-triazoline | I |
| 10. 1-(p-Fluorophenyl)-5-(4-pyridyl)-$\Delta^2$-1,2,3-triazoline | I |
| 11. 1-(p-Methylphenyl)-5-(4-pyridyl)-$\Delta^2$-1,2,3-triazoline | II |
| 12. 1-(m-chlorophenyl)-5-(4-pyridyl)-$\Delta^2$-1,2,3-triazoline | II |
| 13. 1-(phenyl)-5-(2-pyridyl)-$\Delta^2$-1,2,3-triazoline | II |
| 14. 1-(p-Chlorophenyl)-5-(2-pyridyl)-$\Delta^2$-1,2,3-triazoline | II |
| 15. 1-(m-Nitrophenyl)-5-(2-quinolyl)-$\Delta^2$-1,2,3-triazoline | II |
| 16. 1-(p-trifluoromethylphenyl)-5-(4-pyridyl)-$\Delta^2$-1,2,3-triazoline | I |

As shown in the above table, the most potent compounds are compounds 9, 10 and 16 which are the only three compounds of Class I. In addition, compounds 7 and 12 in Class II are also effective anticonvulsant compounds because they give 100% protection at 600 and 300 mg/kg, respectively, without any signs of neurological deficit. Thus, these five compounds represent the preferred embodiments of the anticonvulsant compositions of this invention. Compound 9 which is 1-(para-chlorophenyl)-5-(4-pyridyl)-$\Delta^2$-1,2,3-triazoline and compound 16 which is 1-(p-trifluoromethylphenyl)-5-(4-pyridyl)-$\Delta^2$-1,2,3-triazoline are the most preferred compounds of this invention.

As indicated above while various preparative reactions are known for the triazolines of the invention, the diazo-alkane-imine reaction of the following equation 1 and the azide-olefin cycloaddition reaction of the following equation 2 are generally preferred for 1,2,3-triazoline synthesis:

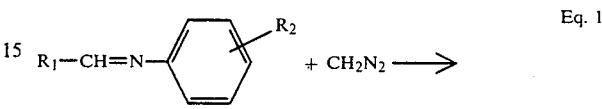

Eq. 1

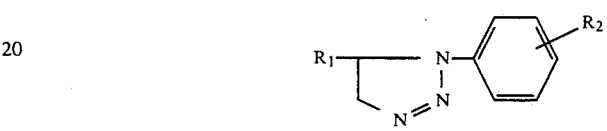

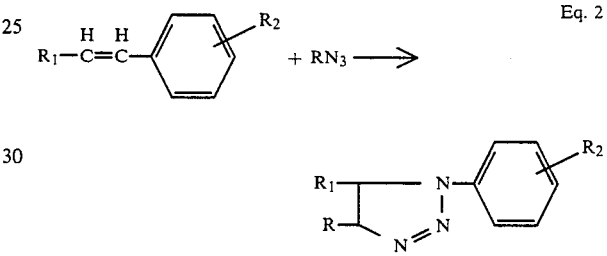

Eq. 2

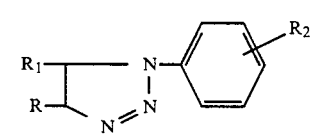

Since Schiff bases (imines) bearing a range of aromatic or heterocyclic substitutents can be readily prepared, the CH$_2$N$_2$-imine reaction is particularly suited for the synthesis of the 1,5-substituted triazolines in this patent application. As pointed out above, this addition is preferably carried out in aqueous dioxane solutions according to the applicant's previous publications. In a typical preparation, the Schiff base is dissolved in a cold, freshly prepared solution of CH$_2$N$_2$ in wet dioxane. The reaction mixture is then allowed to stand at 15°–20° C. for 2–4 days in the case of the reactive anils and 6–7 days in the case of the slow reactions. At the end of this period, the mixture is cooled and diluted with water to precipitate the triazoline adduct.

The CH$_2$N$_2$ for the reaction is prepared conveniently from N,N'-nitrosomethylurea in the same manner that undistilled ethereal solutions are obtained, but using 1,4-dioxane in place of diethyl ether. Dioxane is the solvent of choice because of its easy miscibility with water and the ease with which it can be substituted for diethyl ether. The CH$_2$N$_2$ solution thus obtained contains water in sufficient amounts to catalyze the reaction and is used immediately.

The Schiff bases are prepared using standard procedures by heating a mixture of the appropriate adehyde and amine in ethanol or alternatively by heating the mixture in benzene followed by azeotropic removal of the water, the latter being a more suitable procedure in difficult cases.

The anticonvulsant compounds of the present invention may be administered to animals or humans at doses ranging from about 30 mg/kg up to about 300 mg/kg. Preferred levels of administration range from about 30 mg/kg up to 100 mg/kg. The active ingredients or compounds of this invention may be administered in any desired form by injection or in the oral form. Conventional adjuvents and carriers may be employed in combination with about 0.001 to 2.0 wt.% of the active ingredient. Thus the anticonvulsant compositions of this invention may be administered in pill form or by injection. As indicated above, the dosage rate ranges from about 30 mg/kg up to about 300 mg/kg.

The following examples are presented to illustrate the invention but it is not to be considered as limited thereto. In the examples and throughout the specification, parts are by weight unless otherwise indicated.

EXAMPLE 1

Using the reaction of Equation 1 described above involving cycloadditions of diazoalkanes to imines (Schiff bases), the following compounds were prepared. In the following Table 2, melting points and yields are given for new compounds prepared.

TABLE 2

| Compound | M. pt. °C. | Yield % |
|---|---|---|
| 1. 1-m-trifluoromethylphenyl-5-(o-chlorophenyl)-$\Delta^2$-1,2,3-triazoline | 49–51 | 77 |
| 2. 1-(p-Triflouromethylphenyl)-5-(o-chlorophenyl)-$\Delta^2$-1,2,3-triazoline | 83–86 | 80 |
| 3. 1-(p-Ethylphenyl)-5-(o-chlorophenyl)-$\Delta^2$-1,2,3-triazoline | 44–46 | 48 |
| 4. 1-(m-Chlorophenyl)-5-(o-nitrophenyl)-$\Delta^2$-1,2,3-triazoline | 90–92 | 60 |
| 5. 1-(m-Nitrophenyl)-5-(2,4-dichlorophenyl)-$\Delta^2$-1,2,3-triazoline | — | — |
| 6. 1-(p-Bromophenyl)-5-(2,6-dichlorophenyl)-$\Delta^2$-1,2,3-triazoline | 156 | 75 |
| 7. 1-(Phenyl)-5-(4-pyridyl)-$\Delta^2$-1,2,3-triazoline | — | — |
| 8. 1-(p-Ethoxycarbonyl)-5-(4-pyridyl)-$\Delta^2$-1,2,3-triazoline | — | — |
| 9. 1-(p-Chlorophenyl)-5-(4-pyridyl)-$\Delta^2$-1,2,3-triazoline | — | — |
| 10. 1-(p-Fluorophenyl)-5-(4-pyridyl)-$\Delta^2$-1,2,3-triazoline | 139–141 | 72 |
| 11. 1-(p-Methylphenyl)-5-(4-pyridyl)-$\Delta^2$-1,2,3-triazoline | — | — |
| 12. 1-(m-chlorophenyl)-5-(4 pyridyl)-$\Delta^2$-1,2,3-triazoline | 109–110 | 80 |
| 13. 1-(phenyl)-5-(2-pyridyl)-$\Delta^2$-1,2,3-triazoline | 84–85 | 24 |
| 14. 1-(p-Chlorophenyl)-5-(2-pyridyl)-$\Delta^2$-1,2,3-triazoline | — | — |
| 15. 1-(m-Nitrophenyl)-5-(2-quinolyl)-$\Delta^2$-1,2,3-triazoline | — | — |
| 16. 1-(p-trifluoromethylphenyl)-5-(4-pyridyl)-$\Delta^2$-1,2,3-triazoline | 149–150 | 58 |

These compounds were identified through their elemental analyses, characteristic melting point (they decompose at their melting point with vigorous evolution of nitrogen), and NMR spectra, which exhibits an ABC pattern in the 4.5 to 5.0 ppm region for the three protons at positions 4 and 5.

These compounds were then evaluated in accordance with the methods set forth above for anticonvulsant characteristics. The results are set forth in Table 1 above. As pointed out with respect to Table 1, the compounds demonstrate anticonvulsant activity in either the MES test or the scMet test or both. Compounds of Class I demonstrate this activity at doses of 100 mg/kg or 30 mg/kg without signs of neurological deficit and thus have an estimated protective index of greater than 1.

EXAMPLE 2

One of the compounds, compound 9 which is 1-(para-chlorophenyl)-5-(4-pyridyl)$\Delta^2$-1,2,3-triazoline, was evaluated for further study to provide additional information as to its general profile of anticonvulsant activity.

Thirty minutes after administration, compound 9 of this invention exhibited anti-maximal electroshock (MES) activity at 300 mg/kg and anti-Metrazol activity at 100 mg/kg. Rotorod toxicity was not seen in animals given up to 300 mg/kg of the test substance. Four hours after administration, the compound was ineffective by the MES test (although the tonic extension was slow) at 300 mg/kg; however, anti-Metrazol activity was present at this dose level. Thus, the profile of anticonvulsant activity of compound 9 was characterized by the ability to modify maximal electroshock seizure pattern and to elevate the Metrazol seizure threshold in nontoxic doses. Accordingly, the compound was subjected to Phase II Anticonvulsant Quantification in Mice i.p., Phase III Toxicity Profile in Mice i.p., Phase IV Anticonvulsant Quantification in Mice p.o., Phase V Antiepileptic Drug Differentiation in Mice i.p., and Phase VI Anticonvulsant Quantification in Rats p.o. The results obtained provided the basis to compare the anticonvulsant activity and toxicity of compound 9 with those of clinically useful antiepileptic drugs.

In this experiment male albino mice (CF No. 1 strain; 18 to 25 g wt) obtained from Charles Rivers, Wilmington, Mass., and male albino rats (Sprague Dawley, 100 to 150 g wt) obtained from Simonsen, Gilroy, Calif., were used as experimental animals. All animals were allowed free access to both food (S/L Custom Lab Diet-7) and water, except when they were removed from their cages for the experimental procedure.

Compound 9 was compared with four prototype antiepileptic agents (phenytoin, phenobarbital, ethosuximide, and valproate). Compound 9 was administered in the requisite volume of 30% polyethylene glycol 400; whereas phenytoin, phenobarbital, ethosuximide, and valproate were administered in 0.9% sodium chloride solution. The drugs were administered either orally or intraperitoneally in a volume of 0.01 ml/g body weight in mice and 0.04 ml/10 g in rats. All tests were conducted at the previously determined time of peak drug effect. To determine anticonvulsant potency and toxicity, groups of at least eight mice or rats were tested with various doses of the drug until at least four points were established between the limits of 100% protection or toxicity and 0% protection or toxicity. The dose of drug required to produce the desired endpoint in 50% of animals (ED50) in each test, the dose eliciting evidence of minimal neurological toxicity in 50% of animals (TD50), the 95% confidence interval, the slope of the regression line, and the S.E. of the slope were then calculated by means of a computer program written by NINCDS.

The profile of anticonvulsant activity for each substance was established by five tests: one electrical and four chemical. The electrical test employed was the maximal electroshock seizure pattern test. This test measures the ability of the test drug to abolish the hind limb tonic-extensor component of maximal seizures induced in mice by 50 mA of current delivered for 0.2 seconds or in rats at 150 mA of current delivered for 0.2 seconds; this amount of current is approximately six times the threshold and reveals the ability of the test substance to prevent seizure spread. The four chemical tests include the subcutaneous Metrazol Seizure Threshold Test (sc Met Test), subcutaneous Bicuculline Seizure Threshold Test (sc Bic Test), subcutaneous Picrotoxin Seizure Threshold Test (sc Pic Test), and the subcutaneous Strychnine Seizure Pattern Test (sc Strych Test). Except for the sc Strych Test, these tests measure the ability of anticonvulsants to afford complete protection against threshold seizures induced by the subcutaneous injection of the CD97 of the convulsant agent. The sc Strych Test measures the ability of the test substance to abolish all tonic components of seizures induced by the subcutaneous injection of the CD97 of strychnine. The sc CD97 of Metrazol, bicuculline, picrotoxin, and strychnine in mice is 85, 2.70, 3.15, and 1.20 mg/kg, respectively; the sc CD97 for Metrazol in rats is 70 mg/kg.

The profile of toxicity for each test drug was established by the following procedures: firstly, the minimal neurotoxic dose (TD50) was determined by the rotorod procedure at the time of peak neurotoxic effect. When a normal mouse is placed on a knurled rod one inch in diameter rotating at a speed of six rpm it can maintain its equilibrium for long periods of time. Neurological deficit is indicated by inability of the mouse to maintain its equilibrium for one minute in each of three trials on this rotating rod. Neurological deficit in rats is indicated by ataxia, loss of placing response and muscle tone. Secondly, the overt signs and symptoms of toxicity induced by each prototype agent and test substance were determined by giving two mice either 1TD50, 2TD50's, or 4TD50's and observing and testing them 10, 20, and 30 minutes and 1, 2, 4, 6, 8, and 24 hours after drug administration for the onset, intensity, and type of overt toxicity. These observations also provide preliminary information essential for the subsequent determination of the HD50 and LD50. The HD50 represents the median dose at which 50% of animals lose their righting reflex. The 24-hour LD50 represents the median dose which causes death in 50% of the animals within 24 hours.

Except for bicuculline, all convulsant drugs (Metrazol, picrotoxin, and strychnine) administered to mice were dissolved in sufficient 0.9% sodium chloride solution to make a concentration of 0.85%, 0.032%, and 0.012%, repsectively. Bicuculline was dissolved in 1 ml of warmed 0.1N HCl with the aid of a micro-mixer and sufficient 0.9% sodium chloride solution added to make a 0.027% solution; the solution was used 15 to 45 minutes after preparation. Metrazol (3.5%) was administered to rats in a solution of 0.9% sodium chloride.

All convulsants were administered subcutaneously into a loose fold of skin on the back of the neck in a volume of 0.01 ml/g body weight in mice; Metrazol was injected in a volume of 0.02 ml/10 g body weight in rats. The convulsant drugs were administered at the previously determined time of peak anticonvulsant action of the drug under study. Except for picrotoxin-treated animals, the mice (eight animals/group) were then observed for at least 30 minutes for the presence or absence of a seizure. The animals treated with picrotoxin were observed for periods of 45 to 60 minutes for the presence or absence of a seizure. Except for strychnine, absence of a five-second episode of clonic spasms (threshold seizure) was taken as protection. In the case of strychnine, complete abolition of the hindleg tonic extension was taken as protection.

The results obtained in Phase II Anticonvulsant Quantification studies in mice i.p., are shown in Table 3. It may be seen from the table that the times of peak effect (TPE) of the five compounds range from 15 minutes to 6 hours; except for phenytoin (2 hours by all tests) and compound 9 by the rotorod test (6 hours), the TPE's of the remaining substances vary from 15 minutes to one hour.

TABLE 3

PROFILE OF ANTICONVULSANT ACTIVITY OF INTRAPERITONEALLY ADMINISTERED COMPOUND 9 AND SOME PROTOTYPE ANTIEPILEPTIC DRUGS IN MICE

| Substance | Time of Test (hrs) | Rotorod TD50 (mg/kg) | ED50 (mg/kg) and PI | | | |
|---|---|---|---|---|---|---|
| | | | MES | | sc Met | |
| Compound 9 | 6, ½, ½, | 1132.85 (970.45–1333.28) [7.92] | 257.42 (235.75–297.53) [12.88] | 4.40* | 45.53 (39.00–49.96) [8.75] | 26.02* |
| Phenytoin | 2, 2, 2 | 65.46 (52.49–72.11) [15.23] | 9.50 (8.13–10.44) [13.66] | 6.89 | No protection up to 300 | <0.22 |
| Phenobarbital | ½, 1, 1 | 69.01 (62.84–72.89) [24.67] | 21.78 (14.99–25.52) [14.98] | 3.17 | 13.17 (5.87–15.93) [5.93] | 5.24 |
| Ethosuximide | ½, ½, ½ | 440.83 (383.09–485.34) [18.37] | No protection up to 1000 | <0.44 | 130.35 (112.99–150.45) [10.06] | 3.38 |
| Valproate | ½, ½, ½ | 425.84 (368.91–450.40) [20.84] | 271.66 (246.97–337.89) [12.83] | 1.57 | 148.59 (122.64–177.02) [11.85] | 2.87 |

( ) 95% Confidence interval
[ ]Slope, regression line
*Protective Index (P.I.) = TD50/ED50

With respect to anticonvulsant activity, phenobarbital, the compound of this invention, and valproate had significant anticonvulsant activity in nontoxic doses as measured by both the maximal electroshock seizure (MES; ED50's 21.78, 257.42, and 271.66 mg/kg, respectively) and subcutaneous Metrazol seizure (sc Met; ED50's 13.17, 43.53, and 148.59 mg/kg, respectively) tests. In contrast to the above, phenytoin had significant anti-MES activity (ED50, 9.50 mg/kg) but did not protect against subcutaneous Metrazol seizures. Ethosuximide, on the other hand, was not able to protect against maximal electroshock seizures but had significant anti-Metrazol activity in nontoxic doses (ED50, 130.35 mg/kg).

With regard to minimal neurotoxicity, the compound of this invention was the least toxic (TD50, 1132.85 mg/kg); however, 3 of 8 animals given 1300 mg/kg and 5 of 8 animals given 1500 mg/kg were dead 24 hours after the administration of compound 9. Phenytoin and phenobarbital were the most toxic with TD50's of 65.46 and 69.01 mg/kg, respectively. Ethosuximide and valproate were equitoxic and induced minimal neurological deficit in 50% of mice at doses of 440.83 and 425.84 mg/kg, respectively.

It may also be seen from Table 3 that the protective indices (TD50/ED50=P.I.) by the MES test range from <0.44 for ethosuximide to 6.89 for phenytoin. The P.I.'s of the remaining three compounds (compound 9 of this invention, phenobarbital, and valproate) are 4.40, 3.17, and 1.57, respectively. The P.I.'s of compounds active by the sc Met test range from 2.87 for valproate to 26.02 for the compound of this invention. Phenobarbital and ethosuximide were also effective by the sc Met test with P.I.'s of 5.24 and 3.38, respectively.

Phase III, Toxicity Profile Studies in Mice given 1TD50, 2TD50's, and 4TD50's of Compound 9 intraperitoneally, were also carried out on the compounds. The toxicity profile induced by Compound 9 was characterized by decreased motor activity, ataxia, decreased respiration and cyanosis. In addition to these symptoms, one of two animals given 4TD50's displayed rotorod toxicity. Both mice given 4TD50's of Compound 9 were dead 24 hours after drug administration. One of two animals given 2TD50's was still ataxic and cyanotic at the end of 24 hours. A detailed qualitative description of the profile of acute toxicity in mice (i.p.) of Compound 9 as well as phenytoin, phenobarbital, ethosuximide, and valproate is shown in Table 4. As shown in Table 4, the hypnotic dose 50 (HD50) and lethal dose 50 (LD50) of Compound 9 were 2050.56 and 2132.00 mg/kg, respectively. Thus, the HD50 and LD50 for Compound 9 were significantly higher than those for either phenobarbital (135.45 and 264.70 mg/kg, respectively), phenytoin (178.34 and 229.61 mg/kg, respectively), or valproate (885.33 and 1104.62 mg/kg, respectively). The HD50 of Compound 9 was higher than that for ethosuximide (2050.56 vs 850.61 mg/kg), whereas the LD50's were not significantly different (2132.00 vs 1752.23 mg/kg).

TABLE 4

PROFILE OF ACUTE NEUROTOXICITY OF INTRAPERITONEALLY ADMINISTERED NO. 9 AND SOME PROTOTYPE ANTIEPILEPTIC DRUGS IN MICE

| Name | 1 × TD50 | Profile of Acute Toxicity, Mice i.p. 2 × TD50 | 4 × TD50 | HD50 LD50* (mg/kg) |
|---|---|---|---|---|
| Compound 9 | (1133 mg/kg) Both animals were ataxic beginning at 10 min. One animal had decreased motor activity at 20 min and both had decreased motor activity and respiration with cyanosis at 2 hrs. Both appeared normal at 24 hrs. | (2266 mg/kg) Both animals were ataxic beginning at 10 min. They exhibited decreased respiration with cyanosis beginning at 30 min and decreased motor activity beginning at 2 hrs. One animal appeared normal at 24 hrs while the other remained ataxic and cyanotic at 24 hrs. | (4532 mg/kg) Both animals had ataxia and decreased respiration beginning at 10 min. One animal had decreased motor activity and rotorod toxicity with cyanosis at 10 min. The other animal had decreased motor activity at 2 hrs. Both animals were dead at 24 hrs. | 2050.56 (1591.47–3228.68) [4.27] <br> 2132.00 (1666.11–3368.10) [4.45] |

TABLE 4-continued
PROFILE OF ACUTE NEUROTOXICITY
OF INTRAPERITONEALLY ADMINISTERED NO. 9 AND SOME PROTOTYPE
ANTIEPILEPTIC DRUGS IN MICE

| Name | 1 × TD50 | Profile of Acute Toxicity, Mice i.p.<br>2 × TD50 | 4 × TD50 | HD50<br>LD50*<br>(mg/kg) |
|---|---|---|---|---|
| Pheny-<br>toin | (65 mg/kg) Increased motor activity, slight ataxia, frequent grooming, nervous behavior, and straub tail, animals were not toxic by the rotorod test. | (130 mg/kg) Mild ataxia, periods of sedation, spasms of arching, rolling, straub tail, ptosis, and respiratory depression. Later, spasms reduced and sedation increased. At 24 hrs, toxicity present, other symptoms less pronounced. | (260 mg/kg) Toxic manifestations identical to 2 × TD50. At 1 hr, righting reflex absent, longer periods of sedation, and spasms reduced to head twisting and uncoordinated movements; respiratory depression continued, mice dead at 24 hours. | 178.34<br>(152.93–195.45)<br>[14.03]<br>229.61<br>(216.44–259.10)<br>[15.89] |
| Pheno-<br>barbital | (70 mg/kg) Ataxia with increased motor activity followed by sedation and ptosis with one of two animals toxic by the rotorod test up to 4 hrs. | (140 mg/kg) Ataxia with increased motor activity followed by loss of righting reflex, tremors, reflex scratching, ptosis, sedation and some respiratory depression. Both mice regained their righting reflex at 2 hrs and one of two was still toxic by the rotorod test at 8 hrs. | (280 mg/kg) Ataxia with increased motor activity followed by loss of righting reflex, tremors, reflex scratching, ptosis, sedation, anesthesia with analgesia and respiratory depression. Both animals became cold to touch and cyanotic with increased respiratory depression; death occurred at approximately 3 and 6 hrs. | 135.45<br>(114.90–177.42)<br>[8.41]<br>264.70<br>(241.55–285.52)<br>[15.95] |
| Etho-<br>suximide | (440 mg/kg) Uncoordinated motor activity, reflex scratching, respiratory depression, ataxia. | (880 mg/kg) Uncoordinated motor activity, reflex scratching, loss of righting reflex at 4 mins but regained in 20 mins, hypnosis followed at later time intervals by sedation, ataxia, ptosis, vasodilation and diarrhea. | (1760 mg/kg) Uncoordinated motor activity, respiratory depression, hypnosis and anesthesia followed at later time intervals by cyanosis and death at 24 hrs. | 850.61<br>(751.19–917.93)<br>[16.43]<br>1752.23<br>(1607.02–1866.64)<br>[14.75] |
| Val-<br>proate | (400 mg/kg) Mild ataxia, with one of two mice toxic by the rotorod test. Appeared normal at the end of 4 hrs. | (800 mg/kg) Ataxia, with both animals toxic by the rotorod test, normal respiration and some sedation. Both animals appeared normal at 4 hrs. | (1600 mg/kg) Both animals died. (At 3 × TD50 there was respiratory depression, ptosis, hypnosis but no analgesia. These animals were dead at 4 hrs.) | 885.53<br>(820.86–957.04)<br>[12.46]<br>1104.62<br>(1021.54–1253.66)<br>[11.41] |

*24-hour period

The anticonvulsant activity and minimal neurotoxic dose (TD50) upon oral administration were determined by Phase IV studies, Anticonvulsant Quantification in Mice p.o. The TPE of Compound 9 after oral administration was one-half hour by the anticonvulsant tests; 24 hours was used as the TPE by the rotorod test. The TPE by the rotorod test was significantly different from that obtained after intraperitoneal administration of test Compound 9 (24 hours and six hours, respectively). Except for valproate, the four prototype agents exhibited TPE's that were probably not significantly different from those observed after the intraperitoneal administration of these agents. Valproate had a TPE of one to two hours after oral administration vs one-fourth hour after intraperitoneal administration.

With respect to anticonvulsant activity as measured by the MES test, phenytoin was again the most potent (ED50, 9.04 mg/kg), whereas valproate was the least potent (ED50, 664.80 mg/kg). Compared to phenytoin, phenobarbital was somewhat less potent by the MES test (ED50, 20.09 mg/kg). The test Compound 9, on the other hand, was 1/15 and 1/32 as potent as phenobarbital and phenytoin, respectively, with an ED50 of 290.72 mg/kg. When evaluated by the subcutaneous Metrazol threshold test after oral administration, phenobarbital was the most potent (ED50, 12.59 mg/kg) and valproate was the least potent (ED50, 388.31 mg/kg). The other two compounds (Compound 9 and ethosuximide) were equally potent by the scMet test with ED50's of 152.56 and 192.71 mg/kg, respectively.

By the oral route of administration in mice, ethosuximide and valproate were essentially equitoxic (TD50's, 879.21, and 1264.39 mg/kg, respectively). Phenytoin and phenobarbital were the most toxic with quite similar TD50's (86.71 and 96.78 mg/kg, respectively). Compound 9 was somewhat more toxic than ethosuximide with a TD50 of 704.92 mg/kg; however, several deaths occurred within the dose-range selected for the rotorod regression line (600 and 800 mg/kg, 1 of 8 died; 700 and 1000 mg/kg, 6 and 4 of 8 died).

The P.I. for Compound 9 is 2.42 by the MES test, whereas the P.I.'s for phenytoin, phenobarbital, ethosuximide, and valproate are 9.59, 4.82, <0.44, and 1.90, respectively. The P.I. for Compound 9 by the scMet test is 4.62; whereas those for phenytoin, phenobarbital, ethosuximide, and valproate are <0.29, 7.69, 4.56, and 3.26, respectively. Thus, the P.I. for the Compound 9 substance by the MES test compares very favorably with the P.I. for valproate (2.42 and 1.90, respectively), whereas the P.I. for Compound 9 by the scMet test (4.62) is higher than that for either ethosuximide (4.56) or valproate (3.26).

The results obtained in Phase V evaluation, Antiepileptic Drug Differentiation in Mice, indicated that the profile of anticonvulsant activity of Compound 9 is characterized by its effectiveness by the sc Bic and sc Met tests and its lesser effectiveness by the sc Pic test.

Thus, its profile resembled that of phenobarbital and valproate to a certain extent; all three were effective against sc Met, sc Bic, and sc Pic in nontoxic doses. In contrast to Compound 9 which was not effective against sc Strych, phenobarbital and valproate were effective against strychnine; valproate in nontoxic doses, whereas phenobarbital had to be given in toxic doses in order to protect against this chemical convulsant. Phenytoin, on the other hand, was ineffective against Metrazol, bicuculline, and picrotoxin and was only capable of providing protection in 50% of animals given strychnine. Ethosuximide was effective by the sc Met, sc Bic, and sc Pic tests, and only protected a maximum of 62% of animals by the sc Strych test. However, ethosuximide had to be given in toxic doses to protect against sc Bic seizures. It should also be noted that the P.I.'s for Compound 9 against sc Met and sc Bic are five and fifty times higher, respectively, than those for phenobarbital; the P.I. for Compound 9 by the sc Pic test compares favorably with those for phenobarbital, ethosuximide, and valproate.

In Phase VI studies, Anticonvulsant Quantification in Rats p.o., it was found that the TPE for Compound 9 in this species after oral administration was six hours by the toxicity, MES, and sc Met tests. The TPE of the other four compounds ranged from one-half hour for valproate to five hours for phenobarbital.

With respect to anticonvulsant activity, after oral administration in rats, phenobarbital was the most potent by the MES test (ED50, 9.14 mg/kg), whereas Compound 9 and valproate were the least potent (ED50's, 265.76 and 489.54 mg/kg, respectively). The ED50 of phenytoin by this test was 29.82 mg/kg. When compared on the basis of the sc Met test, phenobarbital was the most potent (ED50, 11.55 mg/kg) and Compound 9 and valproate were the least potent (ED50's, 278.13 and 179.62 mg/kg, respectively). Ethosuximide was somewhat less potent than phenobarbital by this test with an ED50 of 53.97 mg/kg.

With regard to neurotoxicity, phenobarbital was the most toxic (61.09 mg/kg) and ethosuximide and phenytoin the least toxic (TD50's, 1012.31 and >3000 mg/kg, respectively). Valproate and Compound 9 were one-fifth to one-sixth as toxic as phenobarbital with TD50's of 280.26 mg/kg and 393.74 mg/kg, respectively.

In summary of the above results, for Compound 9 and the four prototype agents after intraperitoneal administration in mice and oral administration in mice and rats, it may be stated that, in terms of the profile of anticonvulsant activity, Compound 9 is somewhat similar to that for phenobarbital and valproate. Unlike phenobarbital and valproate, Compound 9 is ineffective after i.p. administration in mice by the sc Strych test, whereas phenobarbital is effective in toxic doses and valproate is effective in nontoxic doses by this test. In terms of rotorod toxicity, Compound 9 is only one-third as toxic as ethosuximide and valproate in this species. After oral administration, Compound 9 is significantly more neurotoxic in rats than it is in mice; there is no significant difference in the anticonvulsant potency of this substance by the MES and sc Met tests in the two species. It should be noted that phenytoin administered orally in higher doses is absorbed only to a limited extent from the gastrointestinal tract of rats. Consequently, no minimal neurotoxicity was observed in this species even in doses up to 3000 mg/kg.

The quantitative toxicity profiles after intraperitoneal administration of Compound 9 and the four prototype agents in mice are summarized in the following Table 5. It may be seen that the time of peak toxicity for Compound 9 by the rotorod and righting reflex tests are 6 and 24 hours, respectively, whereas those for phenytoin are 2 and 12 hours, respectively. The TPE for the other three prototype agents by the rotorod and righting reflex tests range from one-fourth to one hour. This table also shows that the LD50/HD50 and LD50/TD50 ratios for Compound 9 are 1.04 and 1.88, respectively. Thus, the ratios between either the minimal toxic dose and the 24-hour lethal dose or the loss of righting reflex dose and the 24-hour lethal dose for Compound 9 are lower than those for any of the four candidate substances; hence, it would appear that the margin between the minimal toxic dose and the 24-hour lethal dose is probably not satisfactory.

TABLE 5

QUANTITATIVE TOXICITY PROFILE OF INTRAPERITONEALLY ADMINISTERED COMPOUND 9 AND SOME PROTOTYPE ANTIEPILEPTIC DRUGS IN MICE

| Substance | Time of Test (hrs) | Dose 50 (mg/kg) | | |
|---|---|---|---|---|
| | | Lethality | Righting Reflex | Rotorod |
| Compound 9 | 24, 24, 6 | 2132.00 (1666.11–3368.10) [4.45] | 1.04* 2050.56 (1591.47–3228.68) [4.27] | 1.88* 1132.85 (970.45–1333.28) [7.92] |
| Phenytoin | 24, 12, 2 | 229.61 (216.44–259.10) [15.89] | 1.29 178.34 (152.93–195.45) [14.03] | 3.51 65.46 (52.49–72.11) [15.23] |
| Phenobarbital | 24, 1, ¼ | 264.70 (241.55–285.52) [15.95] | 1.95 135.45 (114.90–177.42) [8.41] | 3.84 69.01 (62.84–72.89) [24.67] |
| Ethosuximide | 24, ¼, ¼ | 1752.23 1607.02–1866.64 [14.75] | 2.06 850.61 (751.19–917.93) [16.43] | 3.98 440.83 (383.09–485.34) [18.37] |
| Valproate | 24, ¼, ¼ | 1104.62 (1021.54–1253.66) [11.41] | 1.25 885.53 (820.86–947.04) | 2.59 425.84 (368.91–450.40) |

( ) 95% Confidence interval
[ ]Slope, regression line
*Ratio LD50/HD50 or LD50/TD50

In conducting these tests, it was noted that Compound 9 is very insoluble and difficult to inject. Consequently, it was necessary to administer the high doses required for the righting reflex and 24-hour lethality tests in mice in double the volume. In view of this fact, additional studies were done to determine the effect of this double volume on the time of peak effect of the test substance. These studies indicated that the TPE may actually be between 12 and 20 hours. For example, after the intraperitoneal injection of 1132 mg/kg in mice, 2, 4, 5, 4, and 3 of 8 animals were toxic by the rotorod test 6, 12, 18, 20, and 24 hours, respectively, after administration of the test substance. Moreover, 1, 3, and 4 of the 8 mice were dead at 20, 40, and 46 hours, respectively. Examination of the peritoneal cavity of these animals revealed an unevacuated stomach that was approximately three times normal size; an empty, flaccid small intestine; and a vermiform appendix markedly enlarged from flatus. Rats given 400 mg/kg of the test substance either orally or intraperitoneally presented similar but somewhat milder gastrointestinal symptoms. This cursory gross examination suggests there may be some relation between these gross abnormalities and the onset of toxic symptoms and death. Accordingly, additional pharmacokinetic and pharmacodynamic studies will be done in order to reveal mechanisms that may contribute to the long TPE for neurotoxicity and the abnormally low ratio between the minimal-toxic dose and the 24-hour lethal dose.

The effect of slope on the safety ratio (TD3/ED97) of Compound 9, phenobarbital and valproate indicates that after the intraperitoneal administration of nontoxic doses, the test substance (Compound 9) will protect 97% of mice subjected to either the MES or sc MET test. After oral administration of the test substance in nontoxic doses, the same level of protection is obtained only in mice subjected to the MES test. In this regard, Compound 9 resembles phenobarbital more closely than it does valproate. Moreover, it should be noted that Compound 9 and the prototype agents used for comparison of the safety ratios do not provide 97% protection by the MES and sc Met tests in nontoxic doses after oral administration in rats.

For a candidate drug to be useful in man, it should be adequately absorbed after oral administration. The extent of oral absorption can be determined from the ratio of the oral ED50/i.p. ED50, and should be equal to or less than 4 for adequate absorption. In mice the oral TD50/i.p. TD50 and oral ED50/i.p. ED50 ratios for Compound 9 are 0.62, 1.13 and 3.50, by the rotorod, MES, and sc Met tests, respectively, which suggests that the test Compound 9 is adequately absorbed in mice after oral administration.

For a candidate antiepileptic substance to be useful in the treatment of seizure disorders, its experimental profile of action should compare favorably with that of clinically useful antiepileptic drugs. Such a comparison should include not only the anticonvulsant efficacy (ED50), but also the selectivity of toxic and anticonvulsant effects (slope of the dose-effect regression line), toxicity (LD50, HD50, and TD50), protective indices (TD50/ED50), safety ratios (TD3/ED97), absorption characteristics (oral ED50/i.p. ED50 and oral TD50/i.p. TD50) and the margin of safety (single dose five-day LD50/ED50). An analysis of the data for Compound 9, phenobarbital, ethosuximide, and valproate reveals that Compound 9 compares very favorably with the prototype agents. Moreover, the analysis also shows the relative merits and the disadvantages of Compound 9 compared to phenobarbital and valproate. The merits of the compound are the high P.I.'s derived from the sc Met and sc Bic tests, the high safety ratios in mice (TD3/ED97; MES, 1.13; sc Met, 3.44) and the high 24-hour LD50/ED50 safety ratio by the sc Met test. The disadvantages are related to a lack of selectivity (flat regression lines) by the 24-hour lethality and sc Pic tests and the unfavorable ratios (24-hour LD50/HD50 and 24-hour LD50/TD50).

The invention has been described herein with reference to certain preferred embodiments. However, as obvious variations thereon will become apparent to those skilled in the art, the invention is not to be considered as limited thereto.

I claim:

1. An anticonvulsant composition comprising as the active ingredient an anticonvulsive effective amount of a compound selected from the group consisting of those of the formulae:

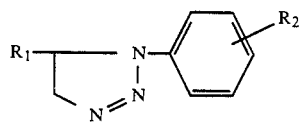

wherein $R_1$ is 4-pyridyl, 2-pyridyl, and $R_2$ is hydrogen, m- or p-trifluoromethyl, p-methyl, p-ethyl, m- or p-chloro, m-nitro, p-bromo, p-fluoro or p-COOR$_3$ wherein $R_3$ is lower alkyl of 1 to 4 carbon atoms, and a carrier.

2. A composition according to claim 1 wherein $R_1$ is 4-pyridyl and $R_2$ is hydrogen.

3. A composition according to claim 1 wherein $R_1$ is 4-pyridyl and $R_2$ is COOC$_2$H$_5$.

4. A composition according to claim 1 wherein $R_1$ is 4-pyridyl and $R_2$ is para-chloro.

5. A composition according to claim 1 wherein $R_1$ is 4-pyridyl and $R_2$ is para-methyl.

6. A composition according to claim 1 wherein $R_1$ is 4-pyridyl and $R_2$ is meta-chloro.

7. A composition according to claim 1 wherein $R_1$ is 2-pyridyl and $R_2$ is hydrogen.

8. A composition according to claim 1 wherein $R_1$ is 2-pyridyl and $R_2$ is para-chloro.

9. A composition according to claim 1, wherein $R_1$ is 4-pyridyl and $R_2$ parafluoro.

10. A composition according to claim 1 wherein $R_1$ is 4-pyridyl and $R_2$ is p-trifluoromethyl.

11. A composition according to claim 1 wherein a sufficient amount of the active ingredient is contained in said composition to provide a dosage amount ranging from about 30 mg/kg to 300 mg/kg.

12. A method for the treatment of convulsive disorders in mammals which comprises administration thereto of an effective dosage amount of a composition of claim 1.

13. A method for the treatment of convulsive disorders in mammals which comprises administration thereto of an effective dosage amount of a composition of claim 4.

* * * * *